United States Patent [19]

Lin et al.

[11] Patent Number: 4,996,374
[45] Date of Patent: Feb. 26, 1991

[54] HYDROGENATION OF ACETOPHENONE

[75] Inventors: Shaw-Chan Lin; Robert N. Cochran, both of West Chester, Pa.

[73] Assignee: Arco Chemical Technology, Inc., Wilmington, Del.

[21] Appl. No.: 451,672

[22] Filed: Dec. 15, 1989

[51] Int. Cl.$^5$ .................. C07C 29/145; C07C 29/143
[52] U.S. Cl. ................................................ 568/814
[58] Field of Search ........................... 568/814, 715

[56] References Cited

U.S. PATENT DOCUMENTS

| | | | |
|---|---|---|---|
| 3,927,120 | 12/1975 | Grane et al. | 568/814 |
| 3,927,121 | 12/1975 | Grane et al. | 568/814 |
| 4,208,539 | 6/1980 | Rashkin | 568/81 X |
| 4,885,409 | 12/1989 | Gardan et al. | 568/834 |

FOREIGN PATENT DOCUMENTS 1204147  9/1986  Japan .................................... 568/814

Primary Examiner—Werren B. Lone
Attorney, Agent, or Firm—William C. Long

[57] ABSTRACT

A process for the hydrogenation of ACP to MBA over a supported palladium catalyst wherein a solvent comprised of ethylbenzene and/or MBA is employed and a small amount of water effective to suppress catalyst deactivation is incorporated in the feed. A further improvement comprises maintaining hydrogen pressure on the catalyst during and between hydrogenation runs.

6 Claims, 2 Drawing Sheets

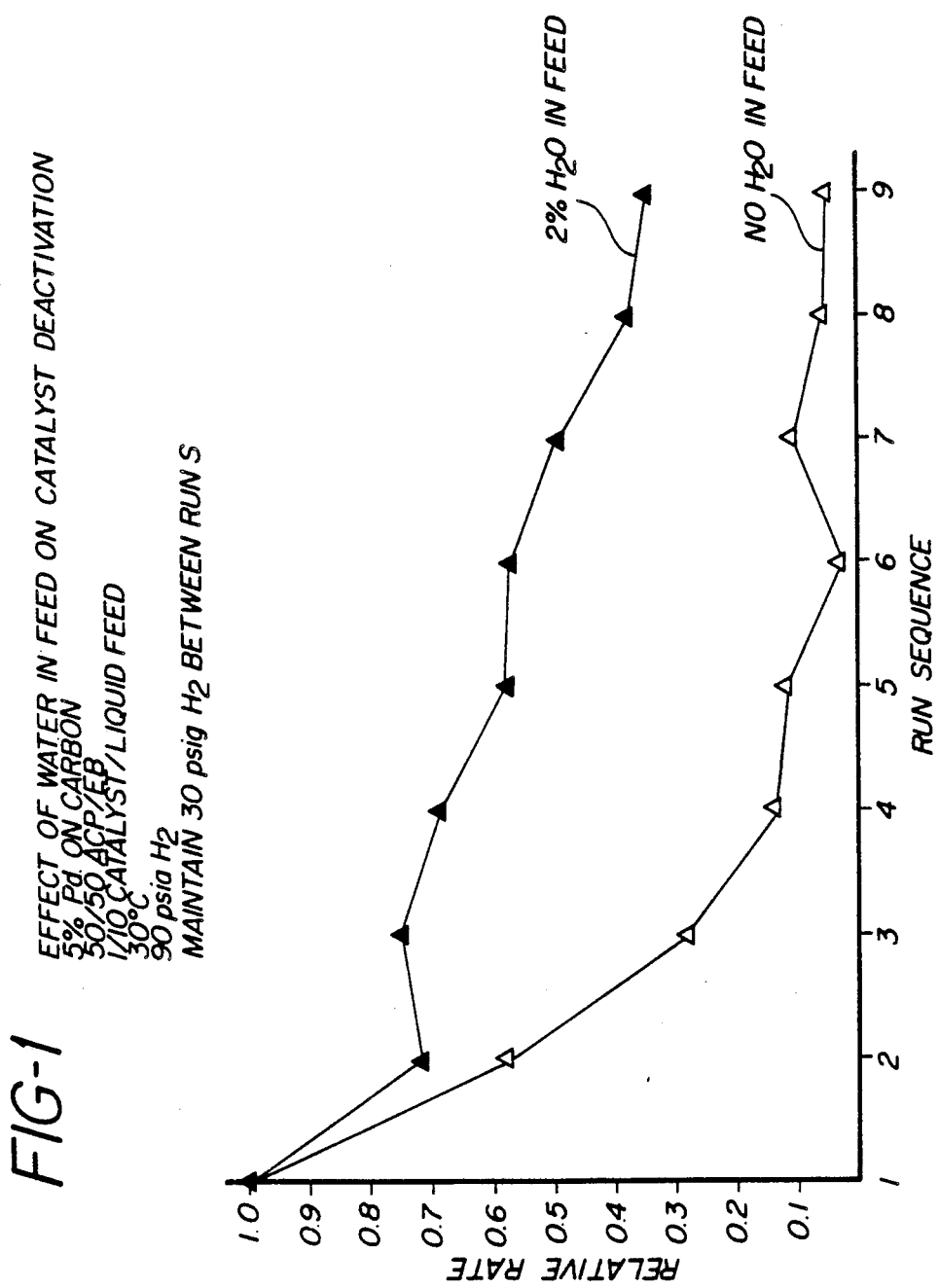

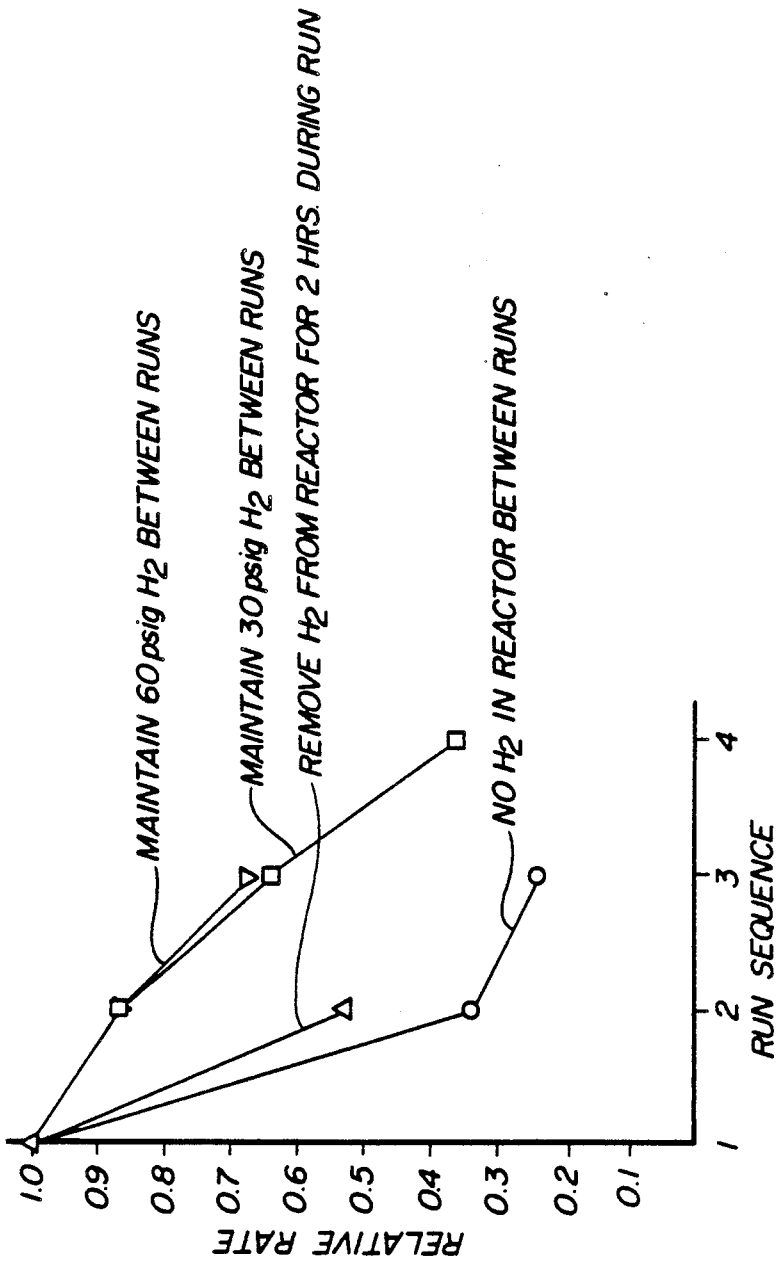

HYDROGENATION OF ACETOPHENONE

BACKGROUND OF THE INVENTION

1. Field of the Invention

The present invention relates to the hydrogenation of acetophenone (herein "ACP") to alpha-methyl benzyl alcohol (herein "MBA") using a supported palladium catalyst, wherein an ethylbenzene and/or MBA solvent is used and catalyst activity is maintained by the incorporation of small amounts of water in the hydrogenation reaction mixture.

2. Description of the Prior Art

Methods have previously been known for the hydrogenation of ACP to MBA. U.S. Pat. Nos. 3,927,120 and 3,927,121 relate to this reaction using copper type catalysts. U.S. Pat. No. 4,208,539 also shows the hydrogenation of ACP to MBA, a barium-copper chromite-zinc catalyst is used.

Hydrogenation conditions tend to be somewhat severe where copper type catalysts are used, and efforts have been made to develop systems which are effective at milder hydrogenation conditions.

Britner, et al., J. Org. Chem., Vol. 24, pages 1855–1857 (1959) show hydrogenation of ACP to MBA using a palladium on carbon catalyst as do Freifelder, et al., J. Pharm. Sciences, Vol. 53, page 967 (1964), Rylander, et al., Engelhard Industries, Inc., Tech. Bull. 8(4), pages 148–153 (1968) and Baltzly, J. Org. Chem., Vol. 41, No. 6, pages 920–936 (1976). Zavgorodnii, et al., React. Kinet. Catal. Lett., Vol. 11, No. 1, pages 31–34 (1979) also show ACP hydrogenation over various supported catalysts.

Although ACP hydrogenation to MBA over supported palladium catalysts has been reported, we have found that a severe disadvantage of such systems is the tendency for the systems to rapidly lose activity.

SUMMARY OF THE INVENTION

In accordance with the present invention, ACP in an ethylbenzene and/or MBA solvent is hydrogenated to MBA over a supported palladium catalyst, and the activity of the system is improved by the incorporation of a small amount of water in the reaction mixture. In addition, the system activity is substantially retained by maintaining hydrogen pressure on the catalyst during periods between reactions, for example, in batch operation when the reaction product mixture is removed and fresh reagents added.

BRIEF DESCRIPTION OF THE DRAWINGS

FIG. 1 shows graphically the effect of addition of a small amount of water on system activity during a succession of batch runs.

FIG. 2 shows graphically the effect of maintaining hydrogen pressure on the catalyst during a succession of batch runs.

DETAILED DESCRIPTION

In accordance with the present invention, an organic feed comprised of ACP together with ethylbenzene and/or MBA solvent has incorporated therein a small amount of water, for example, 1–5 wt. %, and this mixture is hydrogenated over a supported palladium catalyst in order to convert the ACP to MBA. It has been found for this system that the addition of these minor amounts of water substantially reduces the rate of deactivation of the catalyst. A further feature of the invention involves continuously maintaining substantial hydrogen pressure on the catalyst even during periods between runs such as where product is separated and fresh reactant added in order, also, to lessen catalyst deactivation.

Palladium catalysts which are used in practice of the invention are of a known type. Commercially available, palladium on carbon, eg., 5% by wt. Pd on C is especially useful as is commercially available Pd on alumina. Palladium on other supports can be used; the amount of palladium on a support is not critical, generally 1 to about 20 wt % palladium as a percentage of the supported catalyst is usual and can be used.

Practice of the invention is especially advantageous when ethylbenzene is the preferred hydrocarbon solvent, integrated into commercially practiced technology for the coproduction of propylene oxide and styrene monomer as described, for example, in U.S. Pat. No. 3,351,635.

Hydrogenation temperatures generally range from about 20° C. to 150° C., with temperatures of 30° C. to 80° C. being especially preferred. Hydrogen pressures of at least 5 psig are employed, the upper limit being governed by practical limits of the system. A preferred range of hydrogen pressure during the hydrogenation is 70 to 400 psia.

In especially preferred practice, substantial hydrogen pressure is maintained even between hydrogenation runs in order to avoid sharp declines in catalyst activity. Preferred hydrogen pressures between hydrogenation runs are 20 to 60 psia.

The solvent for the hydrogenation is ethylbenzene, MBA or mixtures. Where mixtures are used the relative amounts of ethylbenzene and MBA are not critical and can range from 1% by weight ethylbenzene to 1% by weight MBA. Generally, the solvent comprises 10 to 90% and preferably 30 to 80% by weight of the reaction mixture.

Through practice of the invention, selectivities of 99.5% and higher can be achieved at ACP conversions as high as 90%.

The following examples illustrate the invention.

A series of batch ACP hydrogenations were carried out in a 300 cc slurry reactor equipped with an overhead Magnedrive motor and a six-blade turbine. The reaction conditions were 30° C. and 90 psia hydrogen. The feed consisted of 50/50 ACP/ethylbenzene by weight; the ACP was a commercial material which was distilled to obtain a 5–80% heart cut with a purity of 99.1%; the ethylbenzene had a purity of 99.7%. The catalyst was a commercially available 5 weight percent palladium supported on activated carbon powder available from Engelhard. The catalyst had 850 m²/g surface area and was 50% moist.

In carrying out each run, the fresh catalyst was first charged to the reactor. The reactor was then closed, leak tested and purged with helium to remove air. Liquid feed was pressured into the reactor through a feed vessel using helium and the reactor was heated to 30° C. by means of external furnace. The agitator was controlled at 950 RPM. To start the hydrogenation reaction, the regulated pure hydrogen was fed continuously to the reactor. Pressure in the reactor was maintained at 90 psia hydrogen. At different times liquid samples were drawn from the reactor through a sample line having a 0.5 micron stainless steel filter at one end to prevent the catalyst from leaving the reactor. The samples were analyzed by gas chromatography to determine rate and selectivity. At the end of each run, the liquid product was transferred to a product vessel under hydrogen pressure. Pressure in the reactor was then reduced to 30 psig hydrogen and the successive feed was charged to the reactor. The hydrogen feed was then resumed to carry out the reaction.

The results obtained in various of the batch runs are shown in the following Table 1:

TABLE 1

| RUN | REACTION TEMPERATURE °C. | ACP CONVERSION, % | SELECTIVITY TO MBA, % |
|---|---|---|---|
| 6 | 30 | 90.5 | >99.5 |
| 7 | 30 | 30.9 | >99.5 |
| 8 | 50 | 56.9 | >99.5 |
| 9 | 75 | 35.6 | >99.4 |

The experimental results showed that selectivity in the conversion of ACP to MBA of greater than 99.5% could be achieved at a conversion as high as 90%.

Catalyst deactivation occurred over successive runs, but deactivation was substantially reduced by the incorporation of 2 wt. % water in the feed. Comparative data illustrating this are plotted in FIG. 1, attached. The reaction conditions are given on the Figure. It can be seen that incorporation of small amounts of water in the feed markedly reduced the rate of deactivation.

FIG. 2 shows the effect of hydrogen on catalyst deactivation over a succession of batch runs. Where hydrogen was absent between batch runs, significant activity loss occurred. To demonstrate the importance of hydrogen to catalyst activity, hydrogen was replaced with helium for a 2-hour period during the initial stages of reaction and, as shown, this resulted in 47% activity loss when hydrogen feed resumed. This activity loss was probably due to the absorption of undesirable reaction byproducts on catalyst active sites in the absence of hydrogen. When 30 psig or 60 psig hydrogen was maintained between batch runs, the data show that the rate of deactivation was significantly reduced as indicated in FIG. 2. The run conditions are shown on FIG. 2. From the data plotted in FIG. 2, it can be seen that the maintaining of hydrogen pressure on the catalyst during and between runs has a sharp influence on maintaining catalyst activity.

What is claimed is:

1. The process for the hydrogenation of acetophenone to alpha-methyl benzyl alcohol which comprises contacting a mixture of acetophenone and a solvent comprised of ethylbenzene and/or alpha-methyl benzyl alcohol with hydrogen and a catalyst comprised of palladium supported or carbon or alumina at hydrogenation conditions of 20° to 50° C. and at least 5 psig hydrogen pressure, said mixture also containing 1 to 5 weight percent of water effective to reduce the rate of catalyst deactivation.

2. The method of claim 1 wherein a substantial hydrogen pressure is continuously maintained in the catalyst during and between hydrogenation runs.

3. The method of claim 1 wherein the catalyst is a palladium on carbon catalyst.

4. The method of claim 1 wherein the solvent is ethylbenzene.

5. The method of claim 1 wherein the solvent is alpha-methyl benzyl alcohol.

6. The method of claim 1 wherein the solvent is a mixture of ethylbenzene and alpha-methyl benzyl alcohol.

* * * * *